United States Patent [19]
Zdrojkowski et al.

[11] Patent Number: 5,878,743
[45] Date of Patent: *Mar. 9, 1999

[54] PRESSURE SENSITIVE FLOW CONTROL VALVE

[75] Inventors: Ronald J. Zdrojkowski, Pittsburgh; John R. Starr, Leechburg; Joseph M. Miceli, Pittsburgh, all of Pa.

[73] Assignee: Respironics, Inc., Pittsburgh, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 710,682

[22] Filed: Sep. 23, 1996

[51] Int. Cl.⁶ .................................................. A62B 9/02
[52] U.S. Cl. ............................. 128/204.23; 128/205.24; 128/207.12; 128/207.16
[58] Field of Search .................. 128/203.11, 205.24, 128/202.28, 202.29, 204.23, 207.12, 207.16, 205.27

[56] References Cited

U.S. PATENT DOCUMENTS

| | | | |
|---|---|---|---|
| 3,643,686 | 2/1972 | Koegel | 128/205.24 |
| 3,662,774 | 5/1972 | Johannisson et al. | 128/205.24 |
| 4,229,832 | 10/1980 | Dickson | 2/2.1 |
| 4,579,114 | 4/1986 | Gray et al. | 128/203.11 |
| 4,870,963 | 10/1989 | Carter | 128/205.24 |
| 4,873,970 | 10/1989 | Freidank et al. | 128/207.12 |
| 5,109,840 | 5/1992 | Daleiden | 128/205.24 |
| 5,370,356 | 12/1994 | Pesovic et al. | 251/83 |
| 5,398,673 | 3/1995 | Lambert | 128/202.28 |
| 5,398,714 | 3/1995 | Price | 128/203.11 |
| 5,469,842 | 11/1995 | Flynn | 128/203.11 |
| 5,562,093 | 10/1996 | Gerson | 128/203.11 |
| 5,592,933 | 1/1997 | Zucchi | 128/205.27 |
| 5,598,839 | 2/1997 | Niles et al. | 128/205.23 |

FOREIGN PATENT DOCUMENTS 1204930  10/1958  France ........................ 128/203.11

*Primary Examiner*—John G. Weiss
*Assistant Examiner*—V. Srivastava
*Attorney, Agent, or Firm*—Reed Smith Shaw & McClay

[57] ABSTRACT

A pressure sensitive valve for a positive pressure airway system which allows bi-directional flow with low resistance. When positive pressure from the air generator of the positive pressure airway system is lost, a spring actuated disc moves away from its compressed position to block the outlet of the air generator. By blocking the outlet of the air generator, the path of entry for contaminants is significantly restricted in so doing, an alternate, low resistance path to atmosphere is exposed to allow contaminants to escape.

25 Claims, 6 Drawing Sheets

PRESSURE SENSITIVE FLOW CONTROL VALVE

FIELD OF THE INVENTION

The present invention relates to providing a valve at the outlet of a positive airway pressure (PAP) device such as a continuous positive airway pressure (CPAP) device or bi-level positive airway pressure (BiPAP) device for preventing contaminants from entering the device.

BACKGROUND OF THE INVENTION

Sleep apnea syndrome is due to episodic upper airway obstruction during sleep. As a consequence, there is severe interruption of sleep in the patient. Positive airway pressure devices, such as CPAP, and bi-level positive airway pressure devices have been developed to treat this disorder. CPAP devices deliver positive air pressure to the nasal passages of patients during sleep in order to maintain their airways in a continuously open state. In BiPAP therapy, pressure is applied alternately at relatively higher and lower prescription pressure levels.

A typical PAP device comprises a flow generator (e.g., a blower) which receives air from any suitable source such as a pressurized bottle or the ambient atmosphere. The gas flow from the flow generator is passed via a delivery conduit to a patient interface, such as a mask.

Humidifiers have been developed for use with PAP devices to humidify the air supplied to the patient. A typical humidifier comprises a water reservoir connected in series with the delivery conduit between the flow generator and the patient interface. A problem associated with these humidifiers is the possibility of water from the humidifier entering the PAP device through the delivery conduit and potentially causing damage to the device.

Many PAP devices are also used in combination with a therapeutic gas such as oxygen which is generally delivered at the patient end of the delivery conduit. A problem associated with the use of therapeutic gas is when positive pressure from the flow generator is lost, the therapeutic gas will flow through the delivery conduit to the PAP device potentially causing damage to the device.

The pressure sensitive flow control valve of the present invention has been developed to overcome the problem of water from a humidifier and other contaminants from entering the PAP device by blocking the outlet of the PAP device to restrict the path of entry for the contaminants. Also, the valve prevents the flow of gas, in the absence of positive pressure, back into the PAP device or ventilator by providing a low resistance exit path to atmosphere for any gas or water in the patient circuit.

SUMMARY OF THE INVENTION

The principal advantage of the present invention is realized by providing a pressure sensitive flow control valve at the outlet of a PAP unit to prevent contaminants from entering the PAP unit when positive pressure is lost.

The present invention provides a pressure sensitive flow control valve for a PAP system. While the system is at pressure, the valve allows bi-directional flow with low resistance. When positive pressure is lost, a spring actuated disc moves away from its normal position to block the outlet of the PAP unit. This valve will allow reverse flow as long as there is sufficient pressure. However, if there is not adequate pressure in the valve, indicating that the PAP unit is not functioning, the valve acts much like a one way valve to prevent reverse flow.

The valve of the presently preferred embodiment of the present invention comprises a valve top cap, a valve bottom cap, a valve body disposed between the valve top cap and the valve bottom cap, a valve stem/disc and a spring. All of the components, with the exception of the spring, preferably are polycarbonate components ultrasonically welded together. But those skilled in the art will appreciate that other manufacturing materials and methods are possible.

Other details, objects and advantages of the present invention will become apparent as the following description of the presently preferred embodiments proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

Figure 1:
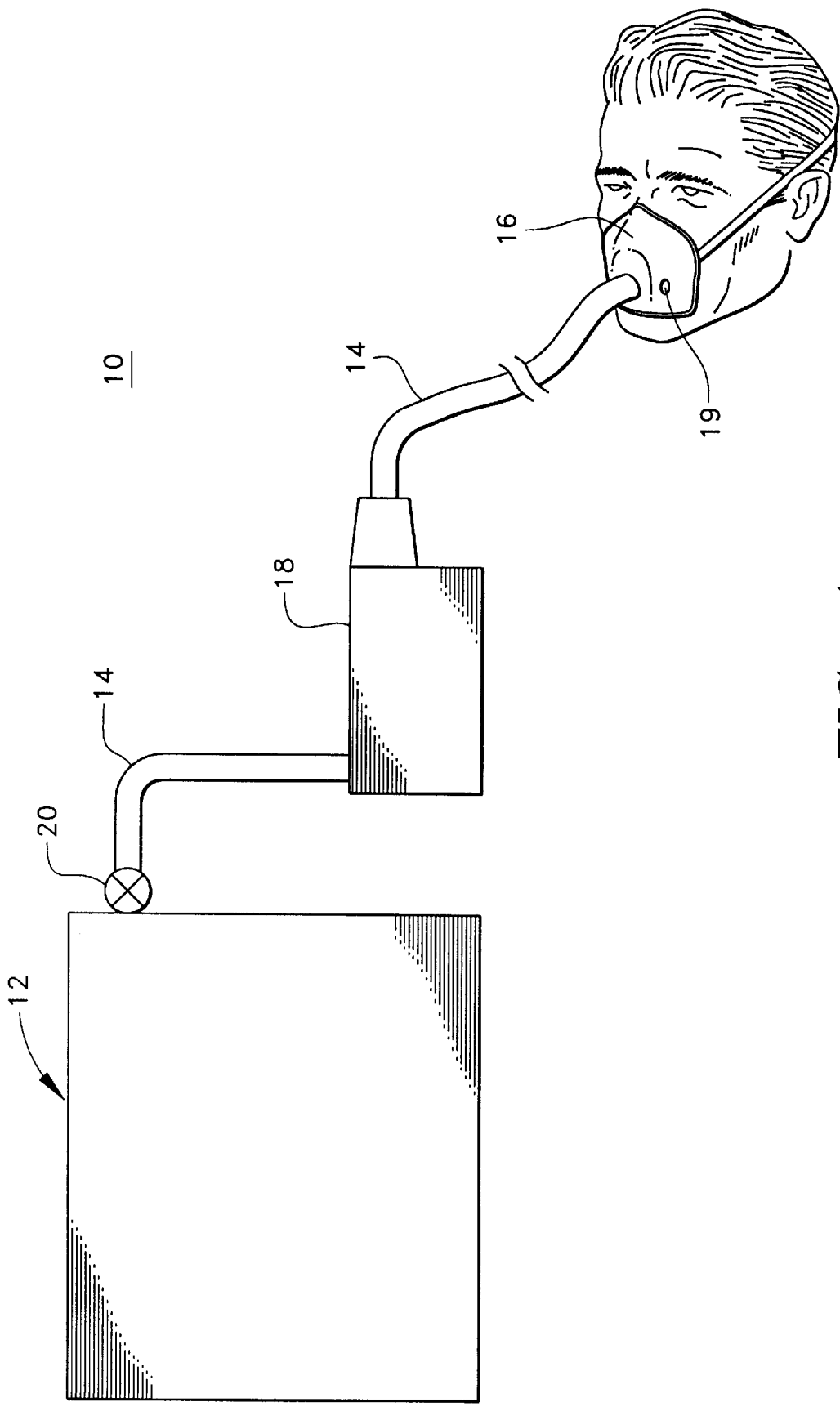
FIG. 1 is a view schematically illustrating a PAP system incorporating the pressure sensitive valve of the present invention.
Figure 2:
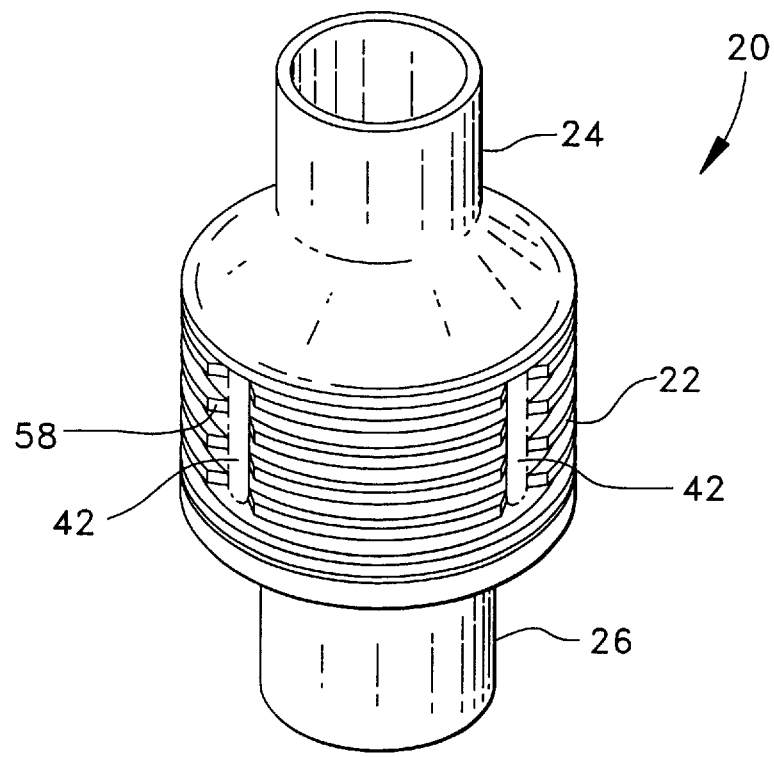
FIG. 2 is a perspective view of the pressure sensitive valve.

Turning to the drawings, a schematic drawing of a PAP system 10 is shown in FIG. 1 which includes a flow generator 12 which delivers gas flow via a delivery conduit 14 to a patient interface 16 such as a mask. Typically a humidifier 18 is disposed in line with the delivery conduit 14 between the flow generator 12 and the patient interface 16. The patient interface 16 may include an inlet 19 for the administration of a therapeutic gas such as $O_2$. In accordance with the present invention a pressure sensitive flow control valve 20 is located at the outlet of the flow generator 12 at the end of the delivery conduit 14 opposite the patient interface 16.

Figure 3:
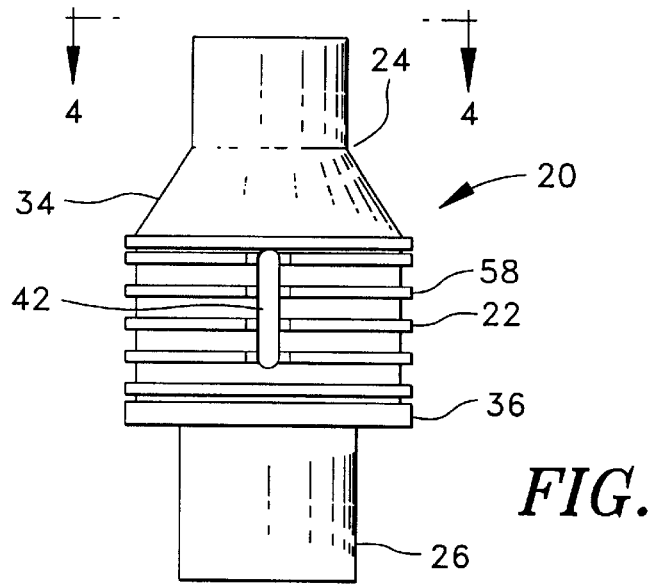
FIG. 3 is a side view of the pressure sensitive valve.
Figure 4:
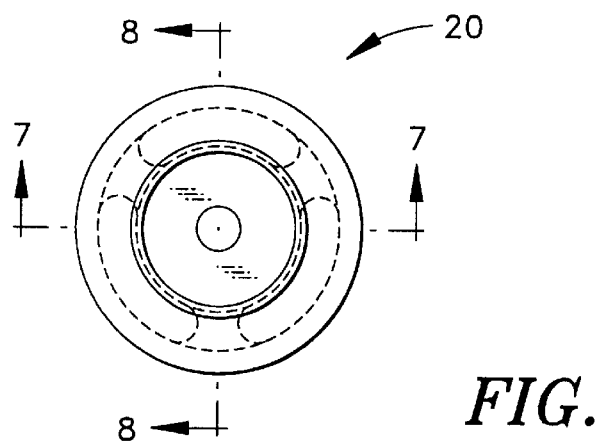
FIG. 4 is an end view of the valve illustrated in FIG. 3 as seen from line 4—4 of that figure.

The details of a pressure sensitive flow control valve 20 in accordance with a presently preferred embodiment of the present invention are shown in FIGS. 2–9 The valve 20 includes a valve body 22, valve top cap 24, a valve bottom cap 26, a spring 28 and a valve stem/disc 30/32 as shown in FIG. 3.

The valve top cap 24, as shown in FIG. 3, is generally cylindrical in shape having a conical end 34 which attaches to the valve body 22. The valve top cap 24 acts as an outlet port to the valve. Valve bottom cap 26, which acts as a supply port to the valve, is also generally cylindrical in shape and has an annular flared portion 36 which attaches to the valve body 22.

Figure 5:
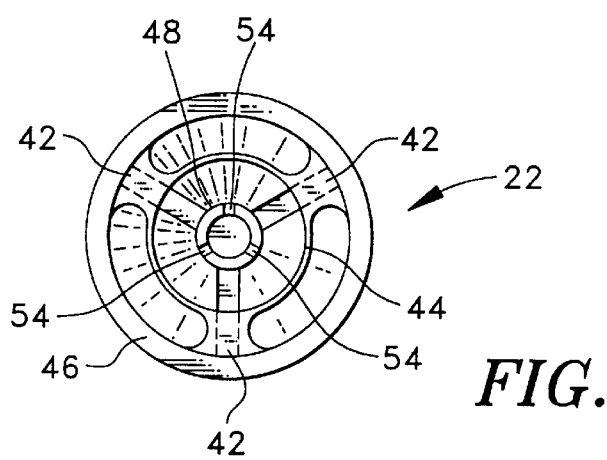
FIG. 5 is an end view of the valve body as shown in the direction of line 5—5 in FIG. 3.
Figure 6:
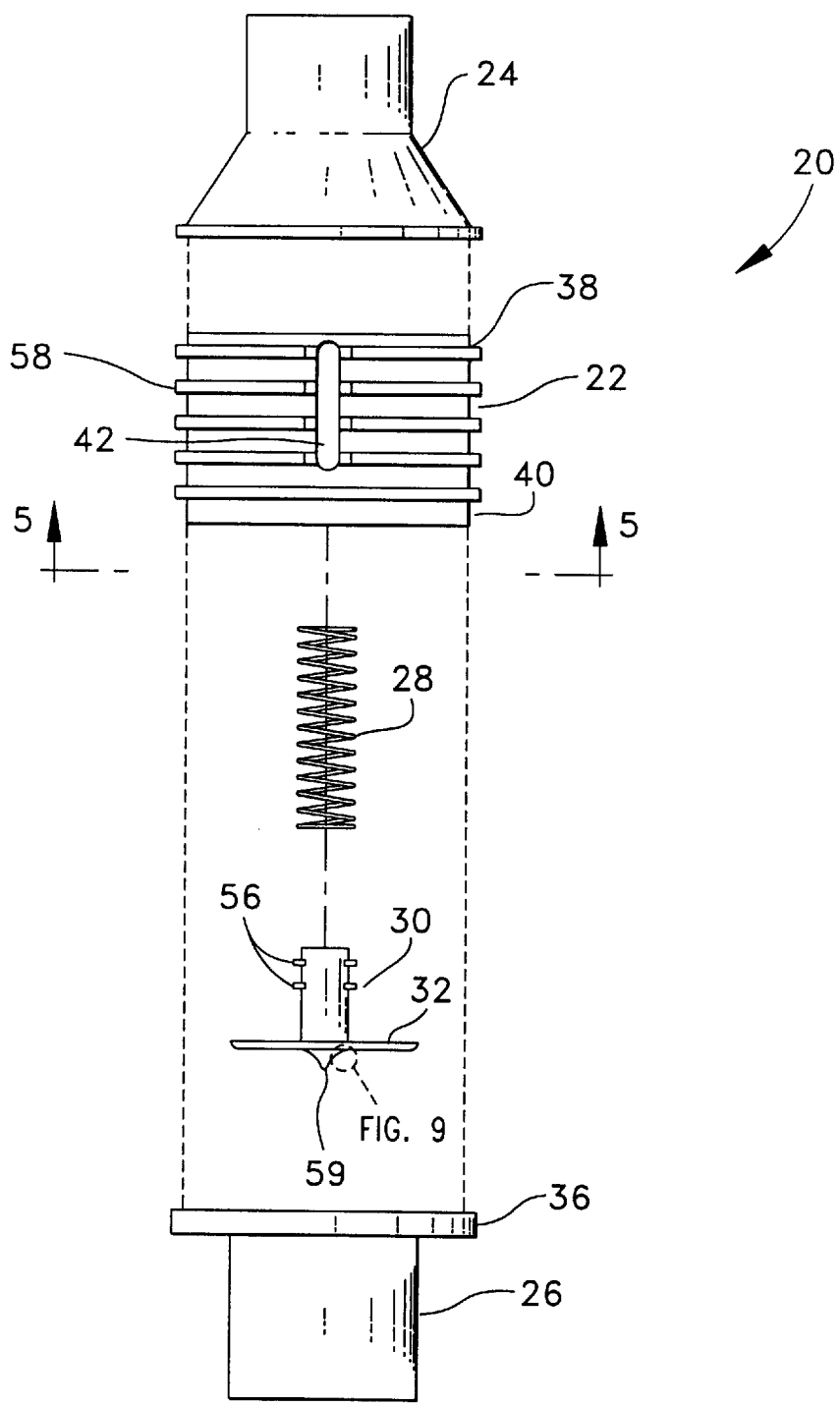
FIG. 6 is an exploded side view of the valve.
Figure 7:
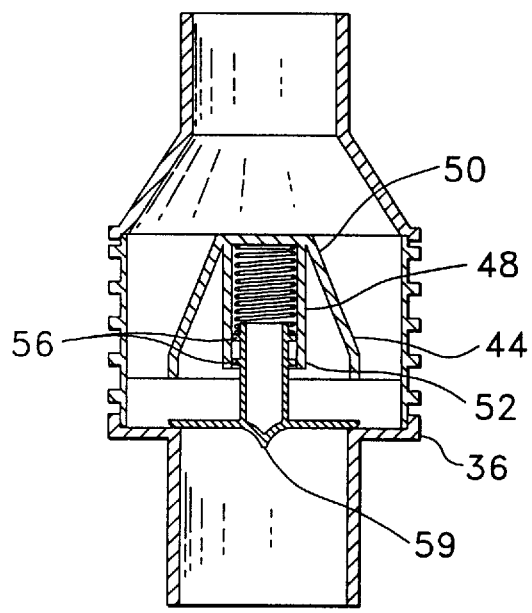
FIG. 7 is a cross-sectional side view of the valve illustrated in FIG. 4 as seen from line 7—7 of that figure illustrating the position of the disc in the absence of positive pressure.
Figure 8:
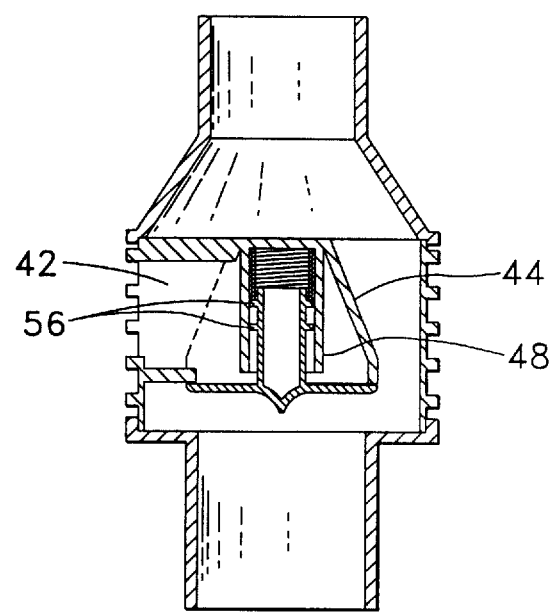
FIG. 8 is a cross-sectional side view of FIG. 4 as seen from line 8—8 of that figure illustrating the position of the disc in the presence of positive pressure.
Figure 9:
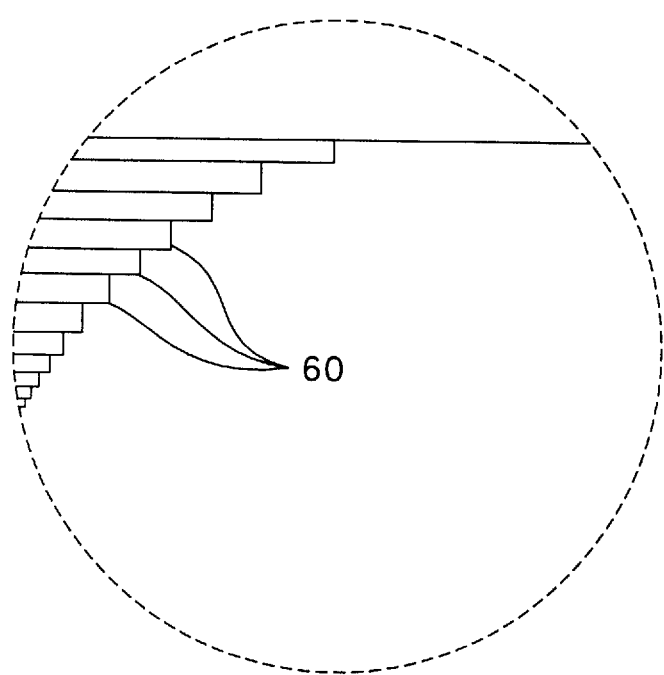
FIG. 9 is a close-up view illustrating details of the disc.

The valve body 22, as seen in FIG. 6, is generally cylindrical in shape and has a top end 38 for attachment to the valve top cap 24 and a bottom end 40 for attachment to the valve bottom cap 26. Exhaust ports 42, as shown in FIGS. 5 and 8, extend radially from an internal conical chamber 44 to the outer surface of the cylindrical body 22. In the preferred embodiment three exhaust ports 42 are shown. Internal conical chamber 44 (FIGS. 5, 7 and 8) extends from the top end to the bottom end and has a central cylindrical guide 48 concentrically disposed within the internal conical chamber 44. The top end 50 of the central cylindrical guide 48 is closed and the bottom end 52 preferably is open such that a spiral spring 28 is insertable inside. The central cylindrical guide 48 preferably has three slits 54 (FIG. 5) which serve as guides for protrusions 56 on the valve stem/disc 30/32. The body 22 also preferably has horizontal ribs 58 on the outside of the body 22 to make it difficult to block the exhaust ports 42 with tape by an untrained user.

The valve stem/disc 30/32 has a stem portion which is adapted to fit inside the cylindrical guide 48 of the valve body 22. An end of the stem portion engages the spring 28 within the cylindrical guide 48, protrusions 56 on the valve stem portion project through the slits 54 in the central cylindrical guide 48 to guide the valve stem as it moves relative to the central cylindrical guide 48. The protrusions 56 are preferably in the form of two rows of fingers but may also be rib-like.

The spring 28 is preferably a spiral spring designed to provide adequately constant force throughout the travel range, giving the valve 20 a sharper response characteristic at precisely the desired pressure condition. The slits 54 are preferably offset 60° from the exhaust ports 42 to prevent unwanted tampering with the internal parts by users.

Integral with the valve stem portion is a valve disc portion located on an end opposite to the spring engaging end. The disc preferably has a centralized conical portion 59 and aerodynamic curves 60 (FIG. 9) to reduce flow resistance.

In normal operation, pressurized air from the PAP unit 10 enters the valve 20 through the valve bottom cap 26 and engages the disc against the work of the spring 28 (FIG. 8). The centralized conical portion and aerodynamic curves of the disk reduce flow resistance such that the pressurized air flows across the disc, around the outside of the internal conical chamber 44 and out through the valve top cap 24 which is connected to the delivery conduit 14 for delivery of the air to the patient through the patient interface 16. While the system is at pressure, the valve 20 also allows reverse flow into the positive airway pressure device. In the absence of pressurized air (FIG. 7), the spring 28 pushes the disc against the annular flared portion 36 of the valve bottom cap 26 to seal off the entry of air or any contaminants into the PAP unit 10. Air or contaminants which enter into the valve 20 when positive air pressure is lost, enter through the valve top cap 24, flow around the outside of the internal conical chamber 44, into the inside of the internal conical chamber 44 to exit the exhaust ports 42 which are open to atmosphere.

While a presently preferred embodiment is shown and described, many variations are within the scope of the present invention. For example, the disc may be formed from a flexible material or formed from a metal such that it may be actuated by pressure as well as magnetic attraction. A floating ball, which is movable back and forth may be used instead of a disk to block the outlet ports to the PAP unit and atmosphere.

Although the invention has been described for the purpose of illustration, it is to be understood that such detail is solely for that purpose and that variations can be made therein by those skilled in the art without departing from the spirit and scope of the invention except as it may be limited to the claims.

What is claimed is:

1. A pressure sensitive flow control valve comprising:

a valve body;

a supply port defined in a first portion of said valve body;

an outlet port defined in a second portion of said valve;

at least one exhaust port defined in a third portion of said valve body; and directing means disposed within said valve body for controlling a flow of gas through said valve body based on a pressure of gas at said supply port and said outlet port relative to atmospheric pressure outside said valve body such that:

(1) as long as said pressure of gas at said supply port and said outlet port are greater than said atmospheric pressure by a predetermined amount, said directing means permits gas to flow from said supply port to said outlet port, provided there exists a pressure differential therebetween, and permits gas to flow from said outlet port to said supply port, provided there exists a pressure differential therebetween, and blocks said at least one exhaust port so that substantially no gas flows therethrough, and (2) if said pressure of gas at said supply port and said outlet port are not greater than said atmospheric pressure by said predetermined amount, said directing means permits substantially all gas entering said valve body through said outlet port to exit said valve body through said at least one exhaust port, thereby substantially preventing elements from passing through said valve body from said outlet port to said supply port.

2. The pressure sensitive flow control valve of claim 1, wherein said directing means also blocks said supply port responsive to said pressure of gas at said supply port and said outlet port not being greater than said atmospheric pressure by said predetermined amount.

3. The pressure sensitive flow control valve of claim 2, wherein said directing means comprises a disc biased by a spring operatively coupled to said valve body.

4. The pressure sensitive flow control valve of claim 3, said directing means further comprising an internal chamber disposed within said valve body, said internal chamber being sized relative to said valve body such that gas flows between an exterior of said internal chamber and a wall defining said valve body, said at least one exhaust port providing a path between an area within said internal chamber an area outside said valve such that, if said pressure of gas at said supply port and said outlet port are not greater than said atmospheric pressure by said predetermined amount, gas entering said valve through said supply port flows around said exterior of said internal chamber before entering said internal chamber and exists said valve through said at least one exhaust port.

5. The pressure sensitive flow control valve of claim 4, wherein said internal chamber is conical in shape and oriented relative to said outlet port such that an apex of said conical shape faces said outlet port to provide an aerodynamic flow of gas around said exterior of said internal chamber.

6. The pressure sensitive flow control valve of claim 4, wherein said disc includes a disc stem that contacts said spring.

7. The pressure sensitive flow control valve of claim 6, further comprising a cylindrical guide disposed within said internal chamber, said cylindrical guide having at least one guide slit defined therein.

8. The pressure sensitive flow control valve of claim 7, wherein said spring is disposed within said cylindrical guide.

9. The pressure sensitive flow control valve of claim 8, wherein said disc stem includes at least one protrusion adapted to engage said at least one guide slit to guide back and forth movement of said disc stem within said cylindrical guide.

10. The pressure sensitive flow control valve of claim 9, wherein said at least one guide slit is offset with respect to said at least one exhaust port.

11. The pressure sensitive flow control valve of claim 4, wherein said disc includes a conical portion and aerodynamic curves to reduce flow resistance.

12. The pressure sensitive flow control valve of claim 1, further comprising ribs disposed on an exterior of said valve body so as to prevent complete blockage of said at least one exhaust port.

13. A pressure sensitive flow control valve comprising:
a valve body having a central cavity defined therein;
a supply port defined in a first portion of said valve body to communicate said central cavity with a first portion of a breathing gas delivery circuit responsive to said first portion of said delivery circuit being operatively connected to said supply port;
an outlet port defined in a second portion of said valve to communicate said central cavity with a second portion of a breathing gas delivery circuit responsive to said second portion of said delivery circuit being operatively connected to said outlet port;
a housing disposed within said central cavity such that gas flows between an exterior of said housing and said valve body, said housing having a first cavity defined therein and a first opening communicating said first cavity with said central cavity;
at least one exhaust port communicating said first cavity of said housing with an ambient atmosphere outside said valve body;
a valve member adapted to substantially prevent gas from flowing from said central cavity to said first cavity responsive to said valve member being in a first position and to permit gas to flow from said central cavity to said first cavity responsive to said valve member being in a second position; and
a biasing mechanism adapted to urge said valve member into said second position responsive to said first pressure in said delivery circuit to which said supply port and said outlet port are operatively coupled being not greater than said atmospheric pressure by a predetermined amount and adapted to permit said valve member to move to said first position responsive to said first pressure in said delivery circuit to which said supply port and said outlet port are operatively coupled being greater than said atmospheric pressure by said predetermined amount.

14. The pressure sensitive flow control valve of claim 13, wherein said valve member further substantially prevents gas from flowing from said central cavity through said supply port responsive to said valve member being in said second position and permits gas to flow from said supply port to said central cavity responsive to said valve member being in a first position.

15. The pressure sensitive flow control valve of claim 13, wherein said valve body has a diameter that is greater than a diameter of a delivery conduit connected to said supply port and said a delivery conduit connect to said outlet port, said diameter of at least a portion of said valve body tapering downward in a direction toward said outlet port.

16. The pressure sensitive flow control valve of claim 13, further comprising external ribs disposed on an exterior portion of said valve body including said at least one exhaust port to substantially prevent obstruction of said at least one exhaust port.

17. The pressure sensitive flow control valve of claim 13, wherein said valve member comprises a valve disc and a valve stem coupled to said valve disc, said valve disc being sized and shaped so as to block gas flow between said central cavity and said supply port responsive to said valve member being in said second position, and wherein said biasing mechanism comprises a spring engaging a portion of said chamber and a portion of said valve member.

18. The pressure sensitive flow control valve of claim 17, further comprising a cylindrical guide disposed within said chamber, said cylindrical guide having at least one guide slit defined therein.

19. The pressure sensitive flow control valve of claim 18, wherein said spring is disposed within said cylindrical guide.

20. The pressure sensitive flow control valve of claim 19, wherein said valve stem includes at least one protrusion adapted to engage said at least one slit to guide axial movement of said valve stem within said cylindrical guide.

21. The pressure sensitive flow control valve of claim 18, wherein said at least one guide slit is offset with respect to said at least one exhaust port.

22. The pressure sensitive flow control valve of claim 17, wherein said valve disc includes a conical portion and aerodynamic curves to reduce flow resistance.

23. The pressure sensitive flow control valve of claim 13, wherein said chamber is conical shaped such that a diameter of said chamber tapers downward in a direction generally toward said outlet port.

24. A breathing gas delivery system comprising:
a flow generator that outputs a breathing gas at a first pressure;
a delivery circuit having a first end operatively coupled to an output of said flow generator and a second end; and
a patient interface operatively coupled to said second end of said delivery circuit for connecting said second end of said delivery circuit to said patient,
said delivery circuit including a pressure sensitive flow control valve comprising:
a valve body,
a supply port defined in a first portion of said valve body and operatively coupled to said delivery circuit such that said supply port receives breathing gas output by said flow generator responsive to said flow generator outputting said breathing gas at least at said first pressure,
an outlet port defined in a second portion of said valve body and operatively coupled to said delivery circuit such that said outlet port provides said breathing gas to said patient interface responsive to said flow generator outputting said breathing gas at least at said first pressure,
at least one exhaust port defined in a third portion of said valve body, and
directing means disposed within said valve body for controlling a flow of gas through said valve body based on said first pressure of gas in said delivery circuit relative to atmospheric pressure outside said delivery circuit such that:

(1) as long as said first pressure said delivery circuit is greater than said atmospheric pressure by a predetermined amount, said directing means permits gas to flow from said supply port to said outlet port, provided there exists a pressure differential therebetween, and permits gas to flow from said outlet port to said supply port, provided there exists a pressure differential therebetween, and blocks said at least one exhaust port so that substantially no gas flows through said at least one exhaust port, and (2) if said first pressure said delivery circuit is not greater than said atmospheric pressure by a predetermined amount, said directing means permits substantially all gas entering said valve body through said outlet port to exit said valve body through said at least one exhaust port, thereby substantially preventing elements from passing through said valve body from said outlet port to said supply port.

25. A breathing gas delivery system comprising:

a flow generator that outputs a breathing gas at a first pressure;

a delivery circuit having a first end operatively coupled to an output of said flow generator and a second end, said flow generator maintaining said delivery circuit at substantially said first pressure during operation of said flow generator; and a patient interface operatively coupled to said second end of said delivery circuit for connecting said second end of said delivery circuit to said patient, said delivery circuit including a pressure sensitive flow control valve comprising:

a valve body having a central cavity defined therein;

a supply port defined in a first portion of said valve body to communicate said central cavity with a first portion of said delivery circuit responsive to said first portion of said delivery circuit being operatively connected to said supply port;

an outlet port defined in a second portion of said valve to communicate said central cavity with a second portion of a breathing gas delivery circuit responsive to said second portion of said delivery circuit being operatively connected to said outlet port;

a housing disposed within said central cavity such that said housing does not move relative to said valve body and such that gas flows between an exterior of said housing and said valve body, said housing having a first cavity defined therein and a first opening communicating said first cavity with said central cavity;

at least one exhaust port communicating said first cavity of said housing with an ambient atmosphere outside said valve body;

a valve member adapted to substantially prevent gas from flowing from said central cavity to said first cavity responsive to said valve member being in a first position and to permit gas to flow from said central cavity to said first cavity responsive to said valve member being in a second position; and a biasing mechanism adapted to urge said valve member into said second position responsive to said first pressure in said delivery circuit being not greater than said atmospheric pressure by a predetermined amount and adapted to permit said valve member to move to said first position responsive to said first pressure in said delivery circuit being greater than said atmospheric pressure by a predetermined amount.

* * * * *